T861008

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED APRIL 1, 1969

861 O.G. 18

729,549

PROTECTIVE COATING COMPOSITION

Robert W. Butler, Wilmington, Del., assignor to Hercules Incorporated, Wilmington, Del., a corporation of Delaware

Filed May 16, 1968. Published Apr. 1, 1969

Class 106—171

No Drawing. 16 Pages Specification

Disclosed is normally solid edible protective coating compositions (forming coatings of increased strength and resistance to moisture and oxygen transmission) comprising normally solid hot melt film-forming material, including (1) normally solid monoglycerides (U.S. Patent 3,113,868), (2) normally solid $C_2$–$C_4$ fatty acid acylated monoglycerides (U.S. Patent 3,247,142), or (3) normally solid poly(oxyalkylene) glycols, or (4) mixtures of two or more of 1–3, and (5) dissolved in said film-forming material normally solid hydroxypropyl cellulose (U.S. Patent 3,278,521). The maximum hydroxypropyl cellulose/film-forming material weight ratio can be about 9/1 but usually ratio is about 1/50–1/1.

The compositions can be prepared by dissolving hydroxypropyl cellulose in molten monoglyceride. They can be used as is or allowed to cool, but preferably articles are coated with the molten composition by dipping or spraying and then allowing to cool and thus solidify. They can also be prepared by dissolving the components in a mutual solvent and evaporating the solvent to form a liquid concentrate. Articles can be coated with the solution or concentrate and the solvent evaporated to solidify the coating.